(12) United States Patent
Gibson et al.

(10) Patent No.: US 6,406,902 B1
(45) Date of Patent: Jun. 18, 2002

(54) HERPES VIRUS PROTEINASE AND METHODS OF ASSAYING

(75) Inventors: D. Wade Gibson, Baltimore, MD (US); Anthony R. Welch, Sunnyvale, CA (US)

(73) Assignee: Johns Hopkins University, Baltimore, MD (US)

( * ) Notice: Subject to any disclaimer, the term of this patent is extended or adjusted under 35 U.S.C. 154(b) by 57 days.

(21) Appl. No.: 09/586,563

(22) Filed: Jun. 2, 2000

Related U.S. Application Data

(60) Division of application No. 09/298,819, filed on Apr. 26, 1999, now Pat. No. 6,077,679, which is a division of application No. 08/251,288, filed on May 31, 1994, now Pat. No. 6,001,967, which is a division of application No. 07/798,776, filed on Nov. 27, 1991, now Pat. No. 5,434,074, which is a continuation-in-part of application No. 07/725,308, filed on Jul. 5, 1991, now abandoned.

(51) Int. Cl.[7] .................................................. C12N 9/50
(52) U.S. Cl. .................... 435/219; 536/23.72; 435/69.1
(58) Field of Search ............................. 536/23.1, 23.72; 435/41, 69.1, 71.1, 320.1, 23, 219

(56) References Cited

U.S. PATENT DOCUMENTS

| 4,772,547 A | 9/1988 | Heimer et al. ................. 435/5 |
| 4,952,674 A | 8/1990 | Keller et al. ................. 530/326 |

FOREIGN PATENT DOCUMENTS

EP            0 514 830            11/1992

OTHER PUBLICATIONS

Robson et al. "Primate Cytomegalovirus Assembly Protein: Genome Location and Nucleotide Sequence" Journal of Virology, vol. 63, No. 2 (Feb. 1989), pp. 669–676. QR355.J65.*

Liu and Roizman, *J. Virol.*, 1993, 67(3):1300–1309.
Baum et al., *J. Virol.*, 1993, 67(1):497–506.
Liu and Roizman, *J. Virol.*, 1991, 65(1):206–212.
Welch and Gibson, *J. Cell Biochem. Suppl.*, 1991, 15:138.
Gibson et al., *J. Virol.*, 1990, 64(3):1241–1249.
Welch et al., *J. Virol.*, 1991, 65(8):4901–4100.
Welch et al., *Proc. Natl Acad. Sci USA*, 1991, 88:10792–10796.
Liu and Roizman, *J. Virol.*, 1991, 65(10):5149–5156.
Bergmeyer, *Methods in Enzymatic Analysis*, vol. V, Enzymes 3, 1984, p. 84.
Ohagi et al., *Nucl. Acids Res.*, 1990, 18(23):7159.
Fling et al., *Mol. Gen. Genet.*, 1991, 227:318–329.
Rich et al., *J. Med. Chem.*, 1990, 33:1285–1288.
Grobelny et al., *Biochem.*, 1989, 28:4948–4951.
Preston et al., *Virology*, 1992, 186:87–98.
Braun et al., *J. Virol.*, 1983, 46(1):103–112.
Braun et al., *J. Virol.*, 1984, 49(1):142–153.
Zweig et al., *J. Virol.*, 1980, 35(3):644–652.
Schenk et al., *J. Virol.*, 1991, 65(3):1525–1529.
Welch et al., *Abstract from 15th International Herpesvirus Workshop*, Aug. 2–8, 1990.

* cited by examiner

Primary Examiner—Jeffrey Stucker
(74) Attorney, Agent, or Firm—Banner & Witcoff, Ltd.

(57) ABSTRACT

A herpes virus proteinase has been found to be encoded by a member of a family of four nested genes in simian cytomegalovirus. Another member of the nested genes encodes the assembly protein precursor, which is a substrate for the proteinase. Homologous genes are found in other herpes viruses. Cleavage sites recognized by the proteinase are identified in cytomegalovirus and are found to be highly conserved in other herpes viruses. Substrates, inhibitors, assay kits, and methods of assaying are provided which rely on the proteinase and its activity.

6 Claims, 7 Drawing Sheets

FIG. 1A

```
                   20                    40                              60
5'-TTGTCCGACACCCCCAGGTTATTGGTGGTCTCCGGGGGGGGAACAGGGGGGTTTGCAGG
                   80                   100                             120
CCTCGGTTAAAGAGCAGCACGCAGATGAGTCTCAAGATCTTGAGTTCTTCCAGCCGCAGG
                  140                   160                             180
GTGTTGAGCGGGCTGTCCCCGGCGACATCTTTTCGCTGATCTG TAATATTA GATGATGGCA
                                                              EndLeuAla>
                  200                   220    APNG1→          240
CAAGTAAAGGAGAATTGCCGGTTCGAACCCGGGCCTCCTCCGTGTTGGACATGGCCGAT
GlnValLysGluAsnLeuProValArgThrArgAlaSerSerValLeuAspMETAlaAsp>
                  260                   280                             300
CCCGTCTACGTCGGGGTTTTTTGGTGCGCTACGACGAGCCTCCCGGAGAAGCTGAGCTG
ProValTyrValGlyGlyPheLeuValArgTyrAspArgProGluProProGlyGluAlaGluLeu>
                  320                   340    5'End                    360
TTTCTGCCCTCGGGGTGTAGACCGCTGGTTGCGCGATTGCCGAGGCCCGTGCCCTG
PheLeuProSerGlyValValAlaAspArgTrpLeuArgAspCysArgGlyProLeuProLeu>
                  380                   400                             420
AATGTCAATCACGACGAGTCGGCGACCGTGGGCTATGTGGGCTCCAGAATGTCCGG
AsnValAsnHisAspGluSerAlaThrValGlyTyrValAlaGlyLeuGlnAsnValArg>
                  440                   460                             480
GCCGGCTTGTTCTGTTTGGGACGTGTTACGTCCCCCAAGTTTCTGGATATCGTTCAAAAA
AlaGlyLeuPheCysLeuGlyArgValThrSerProLysPheLeuAspIleValGlnLys>
```

FIG. 1B

```
            500                520                540
GCCTCGGAAAAATCCGAGTTGGTGTCCCGGGACCTTCCGTCCGAGTCCTCGTTGCGCCG
AlaSerGluLysSerGluLeuValSerArgGlyProProSerGluSerSerLeuArgPro>
            560                580                600
GACGGCGTGTTGGAGTTTCTCAGCGGCAGTTATTCGGGCCTGTCGCTCTCCAGCGCCGA
AspGlyValLeuGluPheLeuSerGlySerTyrSerGlyLeuSerLeuSerSerArgArg>
            620                640                660
GATATAAACGCGCCGATGGCGCCGGGCCGATGCAGAAACAGCGTGCTTCAAACATGTG
AspIleAsnAlaAlaAspGlyAlaAlaGlyAspAlaGluThrAlaCysPheLysHisVal>
            680                700                720
GCTCTGTGCAGCGTGGGCCCGCCGGGCACGTTGGCGGTGTATGGCAGGCAGCCAGAT
AlaLeuCysSerValGlyArgArgGlyThrLeuAlaValTyrGlyArgGlnProAsp>
           740                760                780
TGGGTGATGGAACGTTTCCCGGATCTCACCGAGGCCGAAGCCGGGAAATCAG
TrpValMETGluArgPheProAspLeuThrGluAlaAspArgGluAlaLeuArgAsnGln>
APNG7→
            800                820                840
CTATCGGGAAGTGGGGAAGTTGCCGCGAAGGAAAGTGCGGAATCGTCTGCCGCCGCC
LeuSerGlySerGlyGluValAlaAlaLysGluSerAlaGluSerSerAlaAlaAlaAla>
5'Mid                880                900
GTCGATCCCTTTCAGTCGGATTCGTACGGGCTGTTGGGAACAGTGTGGACGCGCTGTAC
ValAspProPheGlnSerAspSerTyrGlyLeuLeuGlyAsnSerValAspAlaLeuTyr>
            920                940                960
ATTCAAGAGCGTCTCCCTAAGCTGCTATGACAAGCGCTGGTCCGGGTCACGGCTCGG
IleGlnGluArgLeuProLysLeuArgTyrAspLysLeuValGlyValGlyValThrAlaArg>
            980                1000               1020
GAGTCGTACGTGAAAGCCAGTGTTTCGCCCGAGCAGGAGACGTGCGATATTAAGTA
GluSerTyrValLysAlaSerValSerProAlaGluGlnGluThrCysAspIleLysVal>
```

FIG. IC

```
                           1040                       1060         APNG.5→1080
GAAAAGAGCGGGCCGAAGGAGAGCCAGAGCAGAGAGCCACGTACCGACCGAGTCAATGTCTCAC
GluLysGluArgProLysGluProGluGlnSerHisValProThrGluSerMETSerHis>
                      1100                       1120                      1140
CCTATGAGCGCGGTGGCTACTCCGGCCTCGACCGTCGCGGCCTTCTCAGGCGCCGCTG
ProMetSerAlaValAlaThrProAlaAlaSerThrProSerGlnAlaProLeu>
                      1160        3'Mid           1180                     1200
GCGCTGGCCCATGACGGTGTTTATTACCTAAAGACGCTTTTTCTCGCTCATCGGGCC
AlaLeuAlaHisAspGlyValTyrLeuProLysAspAlaPhePheSerLeuIleGlyAla>
                      1220                       1240                      1260
AGTCGTCCCCTGGCCGAGGGCGAGGCGGCCGCGTATCCGGCTGTCCCGCCGCCA
SerArgProLeuAlaGluAlaAlaGlyAlaAlaArgAlaAlaTyrProAlaValProProPro>
      APNG4→          1280                       1300                      1320
CCCGCGTATCCGGTAATGAATTATGAGGACCCCTCCTCAGTCACTTTGACTACAGTGCC
ProAlaTyrProValMETAsnTyrGluAspProSerSerArgHisPheAspTyrSerAla>
                      1340                       1360                      1380
TGGCTGCGGCGGCCAGCTTATGACGCCCGTGCCTCCTCCCCCCGTCATGCCC
TrpLeuArgArgProAlaTyrAspAlaValProLeuProProProProValMetPro>
                      1400                       1420                      1440
ATGCCGTATCCGCAGACGCGACCCCATGATGGAGGAGGCCGAGCGCGCCTGGGAGCGC
MetProTyrArgArgArgAspProMetMetGluGluAlaGluArgAlaAlaTrpGluArg>
                      1460                       1480                      1500
GGGTACGCGCCTTCTGCTTATGACCACTACGTGAACAACGGCTCCTGGTCGCGGAGCCGC
GlyTyrAlaProSerAlaTyrAspHisTyrValAsnAsnGlySerTrpSerArgSerArg>
```

FIG. 1D

```
                1520                1540                1560
AGCGGGCGGCTCAAGAGGAGCCGAAGGGAGCGCGACGCGTCCTCGATGAGGAAGAGGACATG
SerGlyAlaLeuLysArgArgArgGluArgAspAlaSerSerAspGluGluAspMet〉
                1580                1600                1620
AGTTTCCCGGGGAAGCCGACCACGGCCAAGGCTCGGAAAAGACTCAAAGCTCATCACGGG
SerPheProGlyGluAlaAspHisGlyLysAlaArgLeuLysAlaHisHisGly〉
                1640                1660                1680
CGTGATAATAACAACTCTGGGAGCGATGCCAAGGGCGATCGGTACGACGACATTCGGGAA
ArgAspAsnAsnSerGlySerAspAlaLysGlyAspArgTyrAspIleArgGlu〉
                1700                1720                1740
GCGTTACAGGAGCTGAAGCGCGAGATGCTGGCCGTGCGGCAGATCGCGCCACGTGCGCTC
AlaLeuGlnGluLeuLysArgGluMetLeuAlaValArgGlnIleAlaProArgAlaLeu〉
                1760                1780                1800
TTGGCCCCGCACAGCTAGCGACGCCCGTGGCTTCTCCGACAACGACCACGTCGCATCAA
LeuAlaProAlaGlnLeuAlaThrProValAlaSerProThrThrThrThrSerHisGln〉
                1820                1840                1860
GCCGAGGCTAGCGAACCTCAGGCATCGACTGCCGCCGTCGCCCGTCGCCGCTCAACCGCTTCG
AlaGluAlaSerGluProGlnAlaSerThrAlaAlaAlaAlaSerProSerThrAlaSer〉
                1880                1900                1920
TCGCACGGCAGCAAGTCGGCCGAACGCGGTGGTGAACGCCTCGTGTCGCGTTGCGCCT
SerHisGlySerLysSerAlaGluArgGlyValValAsnAlaSerCysArgValAlaPro〉
                1940                1960                1980
CCGTTGGAGGCTGTGAACCCCCTAAGGACATGGTGGACTTGAATCGTCGCCTGTTTGTG
ProLeuGluAlaValAsnProProLysAspMetValAspLeuAsnArgArgLeuPheVal〉
                2000
GCGGCGTTGAATAAAATGGAATAAAAACTCGTAC-3'
AlaAlaLeuAsnLysMetGluEnd
```

3'End

FIG. 2

| HERPESVIRUS | CONSERVED REGION | |
|---|---|---|
| SIMIAN CMV (COLBURN) | PLPLNVNHDESATVGYV | .... FKHVALCSVGRRRGTLAVYG |
| HUMAN CMV (AD169) | ALPLNI NHDDTAVVGHV | .... FKHVALCSVGRRRGTLAVYG |
| HSV-1 | PLPINVDHRAGCEVGRV | .... FAHVALCA I GRR LGT IVTYD |
| VZV | KI PI NI DHRKDCVVGEV | .... FTHVALCVVGRRVGTVVNYD |
| EBV | PLPLTVEH LPDAPVGSV | .... FDHVSI CALGRRRGTTAVYG |
| ILTV | TI PI NI DH ESSCVVGTV | .... FAHVALCELGRREGTVAI YG |
| | CONSERVED MOTIF 2 | CONSERVED MOTIF 1 |

FIG. 3A

| VIRUS | RECOGNITION/CLEAVAGE DOMAIN |
|---|---|
| SCMV | SKSAERGVVNA ↓ SCRVAPP |
| HCMV | AERAQAGVVNA ↓ SCRLATA |
| HSV-1 | SNAEAG ALVNA ↓ SSAAHVD |
| VZV | HTDTVGQDVNA ↓ VEASSKA |
| EBV | GHHRGKKLVQA ↓ SASGVAQ |
| ILTV | NQESARETVDA ↓ SMPKRLK |
| HHV-6 | AA SPKPS I LNA ↓ S------ |

FIG. 3B

| | |
|---|---|
| COLBURN: | VTARESYVKA ↓ SVSPAEQETC |
| HCMV AD169: | VTERESYVKA ↓ SVSPEARAI L |
| HSV-1: | GIAGHTYLQA ↓ SEKFKMWGAE |
| VZV: | GIMGHVYLQA ↓ STGYGLAR I T |
| EBV: | NI PAESYLK A ↓ SDAPDLQKPD |
| ILTV: | AVYNPKYLQA ↓ NEVI TI GI K E |

FIG. 4
-91
-85 (APNG1)
-49 (APNG.7)
-40 (APNG.5, AP)
Anti-C1

HERPES VIRUS PROTEINASE AND METHODS OF ASSAYING

This is a divisional of Ser. No. 09/298,819, filed Apr. 26, 1999, now U.S. Pat. No. 6,077,679, which is a divisional application of Ser. No. 08/251,288, filed May 31, 1994, now U.S. Pat. No. 6,001,967, which is a divisional application of Ser. No. 07/798,776, filed Nov. 27. 1991, now U.S. Pat. No. 5,434,074 which is a continuation-in-part application of Ser. No. 07/725,308, filed Jul. 5, 1991, now abandoned.

This invention was supported under NIH Research Grants RO1 AI22711 and RO1 AI13718. The United States Government retains certain rights in this invention.

TECHNICAL AREA OF THE INVENTION

This invention relates to the area of herpes virology. More particularly, it relates to a new enzyme and the use of that enzyme as a target for anti-viral therapy.

BACKGROUND OF THE INVENTION

Herpes viruses are large double stranded DNA viruses that are responsible for a number of human diseases including chicken pox, shingles, fever blisters, salivary gland virus disease, and infectious mononucleosis. The seven human herpes viruses that have been described thus far are HSV-1, HSV-2, cytomegalovirus (CMV), Epstein-Barr Virus (EBV), varicella zoster virus (VZV), HHV-6, and HHV-7.

Maturation of herpes virus particles is believed to occur through the formation of a procapsid structure, which acquires DNA and an envelope to become an infectious virion. A herpes virus group-common protein referred to as the assembly protein in CMV, and as p40, VP22a, NCP-3, and ICP35e in HSV-1, is an abundant constituent of the herpes virus procapsid. The assembly protein is phosphorylated and proteolytically processed from a precursor molecule. It is absent from the mature virion, although its fate is unknown. These characteristics of the assembly protein have suggested an analogy between it and the bacteriophage scaffolding protein, which is an essential component for phage assembly but is not found in mature virus particles (Gibson et al. (1991) J. Virol. 64:1241–1249).

The proteolytic processing of the assembly protein has been implicated as a critical step in the maturation of the virus. A temperature sensitive (ts) mutant that is unable to process the HSV assembly protein homolog (p40) is incapable of producing DNA-containing capsids or virions (Preston et al. (1983) J. Virol. 45:1056–1064). Maturational processing of the simian CMV (SCMV) Colburn assembly protein results in loss of its carboxy terminus. (Gibson, 1991, supra.)

Up until the present time the enzyme responsible for the proteolytic maturation of the assembly protein has not been identified. Further, there is a need in the art for new agents for therapeutic treatment of herpes viruses.

SUMMARY OF THE INVENTION

It is an object of the invention to provide a preparation of a proteinase encoded by a herpes virus.

It is another object of the invention to provide a substrate for cleavage by a herpes virus proteinase.

It is yet another object of the invention to provide a kit for measuring activity of a herpes virus proteinase.

It is still another object of the invention to provide a method for measuring activity of a herpes virus proteinase.

It is another object of the invention to provide a recombinant DNA molecule which encodes a herpes virus proteinase.

It is yet another object of the invention to provide an inhibitor of a herpes virus proteinase.

These and other objects of the invention are provided by one or more of the embodiments described below.

In one embodiment of the invention a preparation of the proteinase encoded by a herpes virus is provided, said preparation being free of a intact infectious herpes virus virion DNA.

In another embodiment of the invention substrates for cleavage by a herpes virus proteinase are provided. One substrate comprises a polypeptide containing the amino acid sequence:

$aa_1$-$aa_2$-Ala-$aa_3$ (SEQ ID NO:28–30), wherein $aa_1$ is Val or Leu, $aa_2$ is a polar amino acid, and $aa_3$ is Ser, Val, or Asn, wherein the proteinase cleaves the substrate on the carboxy terminal side of the Ala residue. Another substrate comprises a polypeptide containing the amino acid sequence:

Tyr-$aa_4$-$aa_5$-Ala-$aa_6$ (SEQ ID NO:32), wherein $aa_4$ is Val or Leu, $aa_5$ is Lys or Gln and $aa_6$ is Ser or Asn, and wherein the proteinase cleaves the substrate on the carboxy terminal side of the Ala residue.

In yet another embodiment of the invention a kit is provided for measuring activity of a herpes virus proteinase. The kit comprises a proteinase encoded by a herpes virus, and a substrate for cleavage by said proteinase. The substrate comprises a polypeptide containing the amino acid sequence:

$aa_1$-$aa_2$-Ala-$aa_3$ or Tyr-$aa_4$-$aa_5$-Ala-$aa_6$ (SEQ ID NO:28, 29, 30, or 32)

wherein $aa_1$ is Val or Leu, $aa1_2$ is a polar amino acid, aa, is Ser, Val, or Asn, aa4 is Val or Leu, $aa_5$ is Lys or Gin and $aa_6$ is Ser or Asn, wherein the proteinase cleaves the substrate on the carboxy terminal side of the Ala residue, said kit being substantially free of intact infectious herpes virus.

In still another embodiment of the invention a method is provided for measuring activity of a herpes virus proteinase. The method comprises the steps of: contacting a proteinase encoded by a herpes virus with a substrate for cleavage by said proteinase, said substrate comprising a polypeptide containing the amino acid sequence:

$aa_1$-$aa_2$-Ala-$aa_3$ or Tyr-$aa_4$-$aa_5$-Ala-$aa_6$) (SEQ ID NO:28, 29, 30, or 32)

wherein $aa_1$ is Val or Leu, $aa_2$ is a polar amino acid, $aa_3$ is Ser, Val, or Asn, $aa_4$ is Val or Leu, $aa_5$ is Lys or Gin and $aa_6$ is Ser or Asn, wherein the proteinase cleaves the substrate on the carboxy terminal side of the Ala residue, said step of contacting occurring in the absence of an intact infectious herpes virus virion DNA; and monitoring cleavage of said substrate.

In another embodiment of the invention a recombinant DNA molecule is provided which encodes at least a portion of the herpes virus proteinase, said portion having the ability to cleave a herpes virus assembly protein precursor.

In yet another embodiment of the invention an inhibitor of a herpes virus proteinase is provided. The inhibitor comprises a derivative of the substrate of the herpes virus proteinase. The inhibitor may differ from the substrate in the scissile peptide bond which is carboxyl to the Ala residue.

These, and other embodiments of the invention which will be obvious to one skilled in the art from the disclosure, are described in more detail below. These embodiments provide the art with a promising target for specific anti-viral therapeutic agents, which can be administered to humans and other animals without also impairing normal cellular functions.

BRIEF DESCRIPTION OF THE DRAWINGS

FIG. 1 shows the nucleotide (SEQ ID NO:1) and predicted amino acid (SEQ ID NO:2) sequences of the CMV Colburn genomic region containing the assembly protein gene at the 3' end of a 1,770-base pair open reading frame. The open reading frame, designated APNG1, denotes the beginning of the coding sequence of the proteinase gene, and the open reading frame designating APNG.5 denotes the beginning of the coding sequence of the precursor assembly protein gene. Each of the four designated open reading frames are in frame and are 3' co-terminal.

FIG. 2 shows a comparison of portions of the putative active site domains of the proteinase in CMV Colburn (Motif 1, SEQ ID NO:17; Motif 2, SEQ ID NO:16), located between amino acids 15 and 195 and those in other herpes viruses. Two highly conserved motifs within this region are also identified in human CMV (Motif 1, SEQ ID NO:19; Motif 2, SEQ ID NO:18), herpes simplex virus-1 (Motif 1, SEQ ID NO:21; Motif 2, SEQ ID NO:20), varicella zoster virus (Motif 1, SEQ ID NO:23; Motif 2, SEQ ID NO:22), Epstein-Barr virus (Motif 1, SEQ ID NO:25; Motif 2, SEQ ID NO:24), and infectious laryngotracheitis virus (ILTV) (Motif 1, SEQ ID NO:27; Motif 2, SEQ ID NO:26). The absolutely conserved amino acids are shown in bold type.

FIG. 3A shows the cleavage site in the assembly protein of SCMV located between amino acids $Ala_{557}$ and $Ser_{558}$ (SEQ ID NO:3). This region is shown as compared to homologous and conserved regions in other herpes viruses (HCMV, SEQ ID NO:4; HSV-1, SEQ ID NO:5; VZV, SEQ ID NO:6; EBV, SEQ ID NO:7; ILTV, SEQ ID NO:8; and HHV-6, SEQ ID NO:9). Absolutely conserved amino acids are shown in bold type. The arrow in the sequence denotes the cleavage site.

FIG. 3B shows the cleavage site for release of the herpesvirus proteinase from the primary translation product of the APNG1 gene is located in six herpes viruses between amino acids 234 and 262 (Colburn, SEQ ID NO:10; HCMV AD169, SEQ ID NO:11; HSV-1, SEQ ID NO:12; VZV, SEQ ID NO:13 EBV, SEQ ID NO:14; and ILTV, SEQ ID NO:15). Absolutely conserved amino acids are shown in bold type. The space following the alanine residue denotes the cleavage site.

FIG. 4 shows products of an in vitro transcription and translation of the cloned CMV Colburn assembly protein gene (APNG.5) as well as the cloned proteinase gene (APNG1). Proteins are revealed by their reactivity with antibodies (i.e., Anti-C-1) reactive only with noncleaved assembly protein nested gene products.

DETAILED DESCRIPTION

Figure 5:
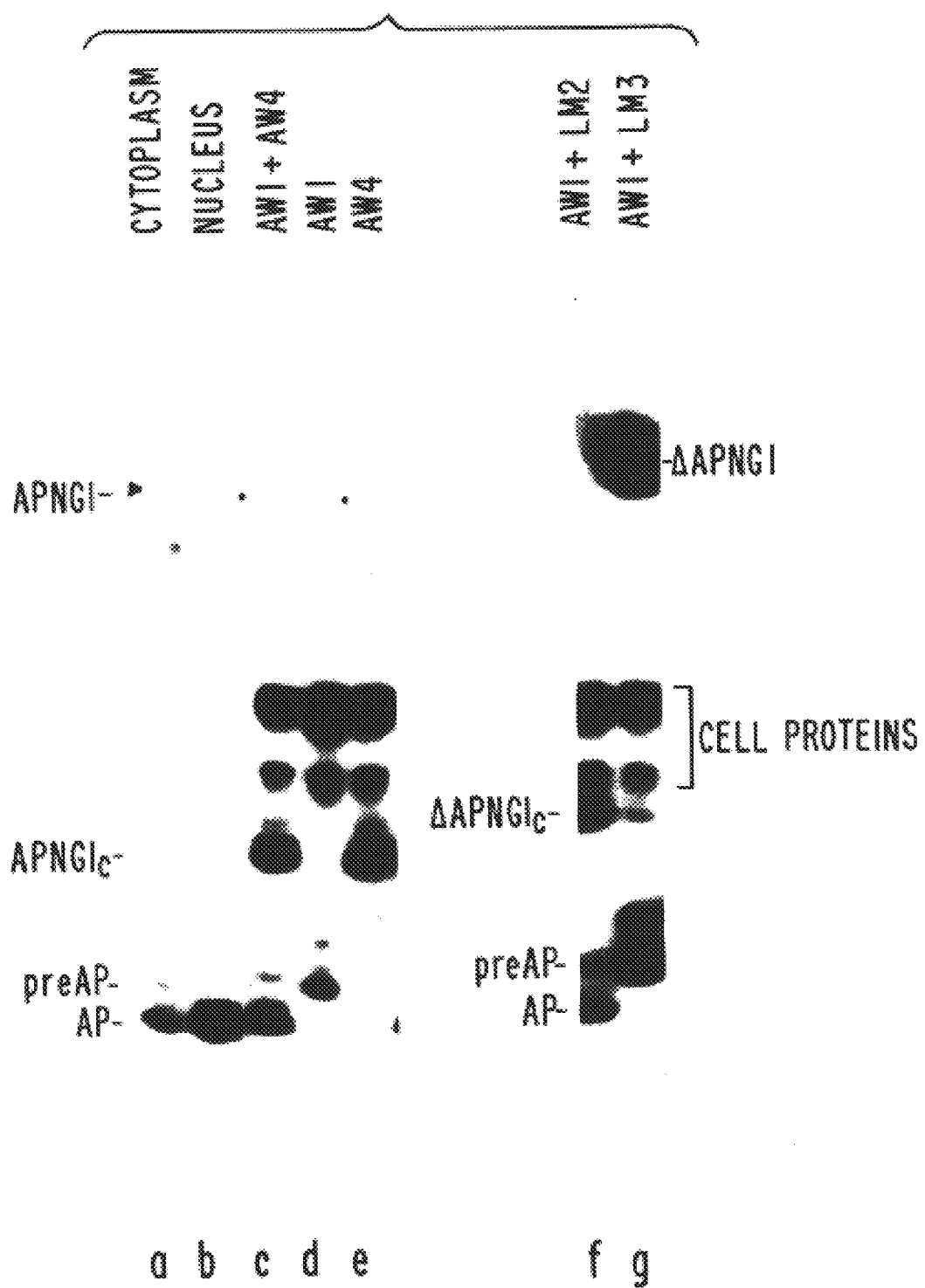
FIG. 5 shows that assembly protein cleavage occurs in cells cotransfected with the genes for the assembly protein precursor (APNG.5/AW1) and for the proteinase (APNG1/AW4).

It is a finding of the present invention that the assembly protein of herpes viruses is maturationally processed by a herpes virus-encoded proteinase. Fascinatingly, the proteinase has been found to be a member of a family of four nested 3' co-terminal genes which includes the assembly protein itself. Each of the genes appears to be transcribed into separate mRNAs.

It appears that proteolytic cleavages may occur in this family of gene products at a number of locations. One such location, which has been identified with certainty, is the cleavage site within the assembly protein precursor itself. This site occurs between the alanine at amino acid position 557 and the serine at amino acid position 558 in the CMV Colburn APNG1 gene product. (Amino acid numbering in this application begins with the first putative initiation codon of APNG1 shown in FIG. 1 as the first underlined methionine codon.) The cleavage site in herpes virus assembly protein precursors have the conserved motif of $aa_1$-$aa_2$-Ala-$aa_3$, wherein $aa_1$ is Val or Leu, $aa_2$ is a polar amino acid, and $aa_3$ is Ser, Val, or Asn. This cleavage site is herein referred to as the assembly protein maturation cleavage site. Another putative cleavage site within this family of nested proteins occurs after the Ala residue of the sequence Tyr-Val-Lys-Ala (SEQ ID NO:40), which occurs at amino acids 246 to 249 in the CMV Colburn APNG1 gene product. This site has been used as the carboxy terminus of a recombinant construct, and the construct has been found to have proteinase activity. This suggests that this site maybe used in vivo for autoprocessing of the proteinase molecule. The cleavage site in the primary translation product of the gene encoding for herpes virus proteinase have the conserved motif of Tyr-$aa_4$-$aa_5$-Ala-$aa_6$, wherein $aa_4$ is Val or Leu, $aa_5$ is Lys or Gln and $aa_6$ is Ser of Asn. This cleavage site is herein referred to as the enzyme release cleavage site. Both the maturation cleavage site and the enzyme release cleavage site in SCMV are highly conserved among herpes viruses as shown in FIGS. 3A and 3B.

SEQ ID NOS 3–9 show the maturational and cleavage site, located between numbered amino acids 11 and 12 in the assembly protein of CMV Colborne, HCMV, HSV-1, VZV, EBV, ILTV and HSV-6, respectively.

SEQ ID NOS 10–15 show the enzyme cleavage site located between numbered amino acid 10 and 11, for the release of the herpesvirus proteinase of CMV Colborne, HCMV, HSV-1, VZV, EBV and ILTV, respectively.

According to the present invention a preparation of proteinase encoded by a herpes virus is provided. The preparation is substantially free of intact infectious herpes virus virion DNA. Virion DNA refers to the DNA which is present in viral particles. Preparations of the present invention can be provided which are totally free of virion DNA because they are produced in cells which have been transfected with a recombinant construct encoding the proteinase. Thus cells producing the proteinase may not ever have been infected with herpes virus. The herpes virus proteinase from cytomegalovirus (CMV, simian strain Colburn) is encoded by a 1,770 base pair gene referred to APNG1 (assembly protein nested gene 1). The nucleotide and amino acid sequence of this gene is shown in SEQ ID NO 1. SEQ ID NO 2 shows only the amino acid sequence shown in SEQ ID NO 1. This gene has homologs in human CMV (HCMV, i.e., UL80a) herpes simplex virus-1 (HSV-1, i.e., UL26), varicella zoster virus (VZV, i.e., UL33), Epstein-Barr virus (EBV, i.e., BVRF2), infectious laryngotracheitis virus (ILTV, i.e., p40 gene), and probably in all herpes viruses. A proteinase according to the present invention may be all or an active portion of the APNG1 primary translation product, or its homologs on other herpes viruses. As previously alluded to, not all of the APNG1 primary translation product is necessary for proteinase activity. For example, constructs which have only the first 249 (LM8) or first 280 (LM7) amino acids beginning with the initial methionine codon on the APNG1 gene both demonstrate proteinase activity. Activity is defined as the ability to proteolytically process the assembly protein precursor of herpes virus to the mature assembly protein or to cleave site mimetic substances.

The preparation of proteinase of the present invention may be made in cells by recombinant DNA techniques, but need not be. The protein may be expressed in mammalian cells, as well as in bacterial, yeast, insect cells, and other cell types, as is convenient for a particular application or purpose. Alternatively, the protein can be chemically synthesized, or expressed in vitro using an in vitro transcription and/or translation system. In still another method of obtaining such a proteinase preparation, infected cells can be used as a source material and standard protein purification techniques can be used. Such purification techniques will typically include an affinity separation step (e.g., immunoaffinity; substrate affinity).

The active site domain of the proteinase enzyme has been tentatively identified as the region between and including amino acids 15 (Asp) and 95 (Ser) in the CMV Colburn APNG1 proteinase. This region contains two motifs that are highly conserved among the homologous genes of HCMV, HSV-1, VZV, EBV, ILTV, and probably all herpes viruses. See FIG. 2. These motifs are referred to as conserved motif 1 and conserved motif 2 SEQ ID NOS 17–27 correspond to conserved motif 1 of CMV Colburn, HCMV, HSV-1, VZV, EBV and ILTV, respectively. SEQ ID NOS 16–26 correspond to conserved motif 2 of CMV Colburne, HCMV, HSV-1, VZV, EBV and ILTV, respectively. A recombinant construct of the proteinase gene was made having a 15 amino acid insertion between conserved motifs 1 and 2. This construct had greatly diminished (i.e., less than about 1% of the wild-type level) proteinase activity, which supports the assignment of the active site domain.

The cleavage site in the assembly protein precursor (i.e., the maturation cleavage site) which leads to formation of the mature assembly protein has been defined with particularity. In simian CMV (Colburn) the cleavage site has been defined as occurring between amino acids 557 and 558. The sequence immediately surrounding this site is Val-Asn-Ala-Ser-Cys (SEQ ID NO:41). When the assembly protein sequences of other herpes viruses are compared it is found that this site is well conserved. (See FIG. 3.) The consensus cleavage site appears to require $aa_1$-$aa_2$-Ala-$aa_3$, wherein $aa_1$ is Val or Leu, $aa_2$ is a polar amino acid, and $aa_3$ is Ser or Val. The amino acid represented as $aa_2$ is most often an asparagine residue.

While not wishing to be bound by any particular theory, there is evidence (Welch et al. (1991) Proc. Natl. Acad. Sci. USA, in press) that an additional cleavage site or sites for the proteinase occurs near the middle of the proteinase sequence. It is likely that the proteinase which is responsible for the maturational cleavage of the assembly protein is also involved in self-processing, possibly to create an active form of the proteinase. The carboxyl half of the APNG1 gene product has been identified in transfected cells, indicating that cleavage in the middle of the APNG1 primary translation product is biologically relevant. (See FIG. 5, $APNG1_c$.) Cleavage at this site (i.e., the enzyme release cleavage site) may be required for the life cycle of the herpes viruses. The consensus sequence for this site comprises Tyr-$aa_4$-$aa_5$-Ala-$aa_6$, wherein $aa_4$ is Leu or Val, $aa_5$ is Lys or Gln, and $aa_6$ is Ser or Asn.

Having defined the actual cleavage site in the assembly protein precursor and putative cleavage site in the proteinase, it is now possible to design smaller synthetic moieties which can be used as substrates for cleavage by the herpes virus proteinase. These substrates for cleavage typically comprise a polypeptide having an amino acid sequence which has been shown to be a recognized cleavage site by a herpes virus proteinase. The polypeptides will contain the amino acid sequence $aa_1$-$aa_2$-Ala-$aa_3$ or Tyr-$aa_4$-$aa_5$-Ala-$aa_6$, and most often will contain the amino acid sequence $aa_1$-$aa_2$-Ala-Ser or Tyr-$aa_4$-$aa_5$-Ala-Ser. The substrate is substantially free of the assembly protein precursor or the entire primary translation product of the gene encoding the herpes virus proteinase. This is possible because the entire assembly protein precursor or the entire primary translation product of the gene encoding the proteinase need not be used as a substrate. Synthetic or recombinant substrates can be made which are recognized and cleaved by a herpes virus proteinase. Substrates for the proteinase will typically comprise a polypeptide portion of between about 15 and 25 amino acids. A sufficient number is required for the proteinase to be able to recognize and bind to the cleavable site.

Extraneous amino acids are not desirable because they may cause steric inhibition by formation of three-dimensional structures which block the cleavage site. Substrates which mimic the maturation cleavage site or the enzyme release cleavage site can also be made.

The substrate itself need not be a totally proteinaceous molecule. It may be linked to other moieties and polymers as is convenient. The substrate will typically be used for assaying proteinase activity in cellular extracts or in synthetic proteinase preparations, as described above, as well as for screening for inhibitory substances which block the proteinase cleavage reaction. In one embodiment of the present invention the polypeptide portion of the substrate is linked to a fluorescent moiety and a quenching moiety. Typically these will be linked on opposite ends of the polypeptide. While linked to the polypeptide the fluorescent moiety will not fluoresce due to the proximity of the quenching moiety. However, upon cleavage of the polypeptide, the separation of the two moieties will lead to a loss of quenching and to detectable fluorescence. An example of a similar quenched fluorogenic substrate is taught by Matayoshi, et al. (Science (1990) 247:954–958). There the fluorogenic and quenching moieties employed are 4-(4-dimethylaminophenylazo)benzoic acid (DABCYL) and 5-[(2-aminoethyl)amino]naphthalane1 sulfonic acid (EDANS). As another example of an indicator substrate, a substrate having the cleavage site engineered into a protein, such as β-galactosidase or luciferase, so that cleavage inactivates the activity of the indicator, is mentioned.

In another embodiment of the invention the substrate for cleavage of a herpes virus proteinase is labeled with a radioactive moiety. After exposure of the substrate to the proteinase, the chemical or physical properties of the radioactive species can be determined, specific changes in these properties can be used to monitor cleavage by the proteinase. One such property is size, a reduction in size of the radioactive species indicating cleavage by the proteinase. Alternatively, after exposure of the substrate to the proteinase, the substrate Pan be extracted into a solvent. A change in the extractability of the radioactive species can be used to indicate cleavage of the substrate. In yet another embodiment of the invention an enzyme is linked to the polypeptide comprising the cleavage site. The polypeptide sterically inhibits the activity of the enzyme. However, upon cleavage of the polypeptide moiety the steric inhibition is relieved and the enzyme activity is regained and can be assayed. Increase of enzyme activity therefore is an indication of cleavage. In an alternative embodiment, the substrate for the enzyme which is linked to the polypeptide for cleavage is also linked to the polypeptide for cleavage. Again, the enzyme is sterically inhibited by its linkage to the polypeptide. However, upon cleavage of the polypeptide the steric inhibition is released and the enzyme can interact with its substrate.

Having discovered the proteinase of herpes virus and its particular sites for cleavage (i.e., the maturation cleavage site and the enzyme release cleavage site), a kit can be readily prepared for measuring the activity of a herpes virus proteinase. The kit comprises a proteinase, or portion thereof, encoded by herpes virus and a substrate for cleavage by said proteinase. The substrate for cleavage has the properties described above. Briefly, a substrate for cleavage contains a polypeptide having the amino acid sequence $aa_1$-$aa_2$-Ala or Tyr-$aa_4$-$aa_5$-Ala, and the proteinase cleaves the substrate on the carboxy terminal side of such sequences. The kit is substantially free of intact infectious herpes virus. This purity can be achieved in a number of ways. Preferably, it can be achieved by expressing the proteinase and the substrate for cleavage in a mammalian cell which is free of herpes virus infection. The cleavage of the substrate occurs within the mammalian cell and can be monitored by observation of a change in the size of the substrate, for example. Alternatively, the proteinase and the substrate can be expressed in an in vitro cell-free system, such as a rabbit reticulocyte system, or synthesized chemically. In such cases the two components of the kit can be contacted in vitro and the cleavage reaction observed. The proteinase and the substrate can also be expressed in separate cells of any suitable species. The cells may be either mammalian, bacterial, yeast, insect, or other cell type, as is convenient for the particular application involved. After separately expressing the proteinase and its substrate they can be contacted in vitro to determine an amount of herpes virus proteinase activity.

In another embodiment of the invention, the cleavage reaction can be used diagnostically to test for the presence of a herpes virus. For example, putatively infected cells can be used as a source of proteinase and contacted with a substrate for cleavage. The cleavage of the substrate would indicate the presence in the source of a herpes virus proteinase and therefore of a herpes virus infection.

Also contemplated by the present invention is a method for measuring activity of a herpes virus proteinase. According to the method, a proteinase encoded by a herpes virus is contacted with a substrate for cleavage by the proteinase. The substrate for cleavage has the properties described above. The contacting of the substrate with the proteinase occurs in the absence of intact infectious herpes virus virion DNA; this can be accomplished by using as sources of substrate and proteinase cells which are not infected with a herpes virus. The second step of the method involves monitoring cleavage of the substrate. Such monitoring can be accomplished by determining a change of size of said substrate, for example, by observing an altered mobility of the substrate on an electrophoretic gel matrix or on a chromatography medium. Alternatively, the monitoring can be accomplished by observing a change of fluorescence if the substrate has been labelled with a fluorescent moiety as described above. If the substrate has been labelled with a radiolabelled moiety then the cleavage reaction can be monitored by looking for a change in its physical properties, as described above. In another embodiment a substrate that has been labelled with an enzyme is used and the cleavage reaction is monitored by determining a colorimetric change of a chromogenic substrate for the enzyme. Suitable enzymes for such purposes are known in the art and include β-galactosidase, alkaline phosphatase, and luciferase.

In one embodiment of the method of the present invention, a test substance is also added to the proteinase (or active portion thereof) and substrate to determine the level of inhibition caused by the test substrate. This method can be used as a screen for potential therapeutic molecules. The level of inhibition can be readily determined by measuring the activity of the proteinase in the presence and absence of the test substrate. A significant diminution of the activity of the proteinase in the presence of the test substance indicates a potential anti-herpetic agent.

Inhibitors of the herpes virus proteinase are also provided by the present invention. Typically, these are non-cleavable derivatives of substrates of the proteinase. The inhibitors may comprise a polypeptide portion of about 6 to 12 amino acids and often will mimic the structure of the appropriate substrate for the proteinase. However, the inhibitor may differ from the substrates for the enzyme in having a modification of the scissile peptide bond which is carboxyl to the sequence $aa_1$-$aa_2$-Ala or Tyr-$aa_4$-$aa_5$-Ala. Any modification of this bond can be used which partially inhibits or totally blocks the proteinase cleavage. Such modifications of the scissile peptide bond include replacement by a hydroxyethylamine linkage, a phosphonamide linkage, a carbon fluoride aldehyde, and a dialcohol linkage. Such inhibitors will bind to the proteinase active site domain but will be either totally non-cleavable or cleavable at a much lower rate than a proper substrate. As the cleavage reaction is known to be essential for the formation of herpes virus particles, inhibition of the cleavage reaction can be used as an anti-herpetic therapeutic treatment.

Certain modifications to the inhibitors of the present invention may be desired in order to render them more resistant to proteolysis in the human body or to render them more easily taken up by infected cells. One such modification is to place an amide moiety on the carboxy terminal end of the polypeptide. This reduces the charge of the molecule rendering it more accessible to cells. Another possible modification involves placing a D-tyrosine moiety on the amino terminal end of the inhibitor. This renders the inhibitor less susceptible to proteolysis.

Other inhibitors may now be designed based on the 3-dimensional structure of the proteinase. Typically, X-ray crystallography is used to determine a structure for the enzyme and inhibitors are designed to conform to the determined structure. Since it has been shown that proteinase activity resides within the first 249 amino acids of the CMV Colbourn APNG1 protein, the use of X-ray crystallography to determine the 3-dimensional structure of the amino terminal 249 residues can be used to design inhibitors of this proteolytically active sequence.

Recombinant DNA molecules are also provided by the present invention. These molecules encode at least a portion of the herpes virus proteinase. The proteinase portion retains the ability to cleave a herpes virus assembly protein. Applicants have found that the entire proteinase gene which is transcribed in vivo as a 1.8 kb RNA molecule, is not necessary for expression of proteinase activity. It has been determined that the portion of the APNG1 gene encoding the assembly protein precursor is not needed for proteolytic activity. Portions of the proteinase which comprise only amino acids 1 through 249 have been found to retain proteolytic activity. Further, as discussed above, it is possible that further shortening of the proteinase molecule is possible without loss of proteolytic activity.

EXAMPLES

Example 1

This example provides the sequence of the simian CMV proteinase gene and compares portions of it to other herpes virus sequences.

The XbaI R fragment of strain Colburn CMV DNA was cloned into the plasmid pUC18, and the nucleotide sequence of both strands was determined by the dideoxy nucleotide chain termination method (Sanger et al., Proc. Natl. Acad. Sci. USA (1977) 74:5463–5467) with appropriate DNA oligonucleotide primers and the Sequenase kit (USB, Cleveland, Ohio).

Nucleotide sequence analysis of the CMV (Colburn) genomic XbaI R fragment confirmed the cDNA sequence previously determined for the assembly protein-coding region and revealed that the 930-bp coding sequence for the assembly protein precursor (nucleotides 1072 to 2001) is the 3' end of a 1,770-bp open reading frame (ORF) (nucleotides 232 to 2001) that begins with a methionine and, together with its upstream regulatory region, was designated assembly protein nested gene 1 (FIG. 1). APNG1 includes an upstream potential TATA promoter element, contains three internal potential TATA promoters and three corresponding ATG translational start codons in addition to its own, and is followed by a single downstream polyadenylation signal. This organization indicated that the APNG1 region could give rise to four 3'-coterminal mRNAs able to encode four corresponding in-frame, overlapping proteins. These nested coding sequences are numbered according to their fractional length relative to that of the longest, APNG1. FIG. 1 presents the nucleotide and amino acid sequences of the APNG1 region and shows the positions of (1) proposed TATA promoter elements (italicized and dot underlined), (2) proposed translational start methionines for the coding sequence in each of the nested genes (capitalized and doubly underlined, and the designation of the corresponding assembly protein nested gene (APNG) is indicated above each), (3) the single polyadenylation signal at the 3' end (underlined). The APNG1 (proteinase) gene has homologs in human CMV (HCMV, i.e., UL80a), herpes simplex virus type-1 (HSV-1, i.e., UL27), varicella zoster virus (VZV, i.e., UL33), Epstein-Barr virus (EBV, i.e., BVRF2), and infections laryngotracheitis virus (ILTV, i.e., p40).

At least a portion of the active site domain of the proteinase has now been tentatively identified as the region between amino acids 15 and 195 in the CMV Colburn APNG1 protein. This region contains two motifs that are highly conserved among the homologous genes of HCMV, HSV-1, VZV, EBV, and ILTV, and probably all herpes viruses (FIG. 2). These motifs are referred to as "conserved motif 1" (CM1) and "conserved motif 2". Striking similarities in the spacing of possible active site residues resembling both cysteine (i.e., $His_{47}$, $Cys_{146}$, $His_{142}$) and serine ($His_{47}$, $Asp_{104}$, $Ser_{195}$) proteinases are detected among all six herpes viruses, suggesting that the herpes virus proteinases may have two separate proteolytic activities.

It has been found that an altered form of APNG1 (LM3) which contains a 15 amino acid sequence (the C3 epitope of poliovirus VP2) inserted between CM1 and CM2, has only a trace amount of proteinase activity (i.e., ≦1%) (see FIG. 5, lane g). Insertion of the same sequence into the carboxyl end of APNG1 did not reduce proteinase activity (FIG. 5, lane f). This suggests that the CM1/CM2 region does contain at least a portion of the active site domain of this proteinase.

Furthermore, two subclones of APNG1 were made which expressed portions of the proteinase gene comprising amino acids 1–249 (LM8) and 1–280 (LM7). Both are proteolytically active using assembly protein precursor as a substrate. This, too, supports the active site domain assignment.

Example 2

This example demonstrates the precise cleavage site involved in the maturational processing of assembly protein precursor to assembly protein, as well as the conservation of the site among herpes viruses.

The mature assembly protein was treated with endoproteinase Lys-C or endoproteinase Glu-C (V8 proteinase). Specific peptide products were isolated and subjected to analysis by mass spectrometry. The diagnostic molecular ions identified from HPLC-purified peptides of the Colburn CMV assembly protein were mass 902.5 (Endo-Lys-C fragment, SAERGVVNA) and mass 616.4 (Endo-Glu-C fragment, RGVVNA). Thus the cleavage site is between $Ala_{557}$ and $Ser_{558}$ in SCMV Colburn. This cleavage site is well conserved in HCMV, HSV-1, VZV, EBV, ILTV, and probably in all herpes group viruses (FIG. 3).

Example 3

This example provides proteinase substrate derivatives with altered chemistry at the scissile peptide bond.

Based on the cleavage site sequence, several classes of anti-herpes virus peptide mimetics can be synthesized. These include hydroxyethylamine-, dialcohol-, phosphonamide-, and carbon fluoride aldehyde-derivatives of the scissile peptide bond (i.e., carboxyl to the alanine in the general sequences $aa_1$-$aa_2$-Ala-$aa_3$ and Tyr-$aa_4$-$aa_5$-Ala-$aa_6$, such as:

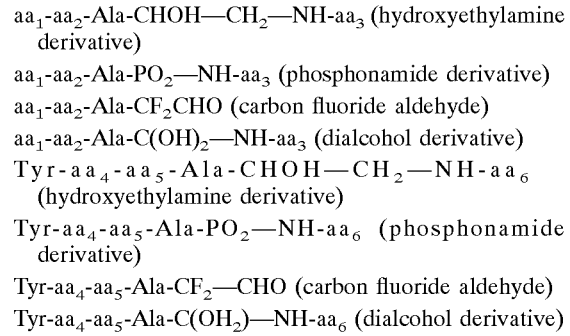

Example 4

This example demonstrates the in vitro transcription and translation of the cloned CMV Colburn assembly protein precursor gene.

The assembly protein precursor gene (APNG.5, see FIG. 1) and the overlapping APNG1 gene were cloned from the simian strain Colburn CMV DNA, using PCR amplification, into a pGEM4Z plasmid to produce plasmids AW2 and AW3, respectively. T7-promoted run-off transcripts of both genes were prepared, and translated in rabbit reticulocyte lysates containing $^{35}$S-methionine. The proteins were separated by electrophoresis in an SDS-containing polyacrylamide gel (10%), electrotransferred onto an Immobilon-P™ membrane and probed with an antiserum to the carboxyl 21 amino acids of the assembly protein precursor (i.e., Anti-C1, see Schenk, et al. (1991) J. Viol. 65: 1525–1529). The resulting protein-antibody complexes were visualized by using $^{125}$I-Protein A. A fluorogram of the blot is shown in FIG. 4. The exposure technique used recorded only $^{125}$I-radioactivity (i.e., Kodak DEF film and black paper between blot and recording Kodak XAR film).

The in vitro translated assembly protein (lane 3, APNG.5/AW2) comigrated with the infected cell assembly protein precursor (i.e., 40-kDa band in lane 5) and was not proteolytically processed in the reticulocyte lysate. The protein product of the APNG1 gene (lane 4) comigrated with the 85-kDa protein present in the Colburn CMV-infected cell cytoplasm (i.e., 85-kDa band in lane 5). Mock infected nuclear and cytoplasmic fractions (lanes 1 and 6) show no evidence of proteins reactive with the Anti-C1 antibody.

Example 5

This example demonstrates that assembly protein cleavage occurs in cells cotransfected with the genes for the assembly protein precursor and for the APNG1 protein.

Human cells were transfected with an expression plasmid containing the gene for the assembly protein precursor (AW1), or with an expression plasmid containing the gene for the APNG1 protein (AW4), or with both plasmids (AW1+AW4). Parallel cotransfections were done using the AW1 plasmid in combination with altered versions of AW4 that contain (1) a 13 amino acid sequence inserted into the carboxyl end of APNG1 (LM2), or (2) a 15 amino acid sequence inserted into the amino end of APNG1 (LM3).

Following transfection the cells were solubilized and the proteins were separated by electrophoresis in an SDS-containing polyacrylamide gel (SDS-PAGE). The resolved proteins were electrotransferred to an Immobilon-P™ membrane and visualized by probing the membrane with an antiserum (Anti-N1) that reacts with the amino end of the assembly protein and with other assembly protein nested gene products (e.g., 85-kDa APNG1 protein). Colburn CMV-infected cell proteins were run as markers. The results of these experiments are shown in FIG. 5.

The assembly protein (AP) and its precursor (preAP) can be seen in the cytoplasmic and nuclear fractions of Colburn CMV-infected cells (lanes a and b, respectively). The precursor form is more abundant in the cytoplasm (lane a) and the mature form is more abundant in the nucleus (lane b).

Cells transfected with only the gene coding for the assembly protein precursor (i.e., plasmid AW1) expressed the precursor form of the assembly protein but no product (lane d). The much less abundant, slightly larger protein is believed to correspond to a protein also detected in infected cells, but present there in vanishingly small amounts.

Cells transfected with only the gene coding for the larger protein of the "assembly protein nested gene family" (i.e., 85-kDa protein product of APNG1 encoded by plasmid AW4) expressed the 85 k-Da protein (APNG1), and a second doublet band believed to represent the carboxyl end of the APNG1 protein (i.e., $APNG1_c$, 45– to 50 kDa in size, lane e).

Cells cotransfected with the assembly protein precursor gene and the APNG1 gene (i.e., AW1+AW4) contained: (1) the APNG1 and $APNG1_c$ proteins encoded by AW4, and (2) predominantly the mature (i.e., cleaved) form of the assembly protein (AP) (lane c). Essentially no precursor form of the assembly protein (preAP) was detected with this serum (Anti-N1) or with an even more sensitive antiserum for the precursor form (i.e., Anti-C1). This finding indicates that cleavage of the precursor in transfected cells is highly efficient.

Cells cotransfected with the assembly protein precursor gene (AW1) and an altered form of the APNG1 gene (LM2, altered at the carboxyl end) that contains a 45 bp insert at the single APNG1 DraI site, encoding the polio virus VP2 C3 epitope (Charbit, et al., 1986, EMBO J., vol. 5, pp. 5029–3038) contained: (1) a higher molecular weight form of APNG1 (ΔAPNG1, indicated by dot to left of lane f) resulting from the inserted 15 amino acids of VP2 C3, (2) a correspondingly larger form of the carboxyl end of the APNG1 protein (i.e., $\Delta APNG1_c$), and (3) only the mature (i.e., cleaved) form of the assembly protein (AP)(lane f). The band close to the position of the assembly protein precursor (i.e., preAP) in lane 4 is not reactive with Anti-C1 and is believed to correspond to the processed form of the slightly larger, low abundance protein expressed by AW1 and mentioned above.

Cells cotransfected with the assembly protein precursor gene (AW1) and an altered form of the APNG1 gene (LM3, altered at amino, N'-end) that contains a 45 bp insert (VP2 C3) at the single APNG1 EcoRV site, located between the highly conserved motifs CM1 and CM2, contained: (1) a higher molecular weight form of APNG1 (ΔAPNG1, indicated by arrow to left of lane g) resulting from the inserted 15 amino acids of VP2 C3, (2) a weak band at the position of $\Delta APNG1_c$, but corresponding in size to the band in lane f because the carboxyl cleavage at Val-Asn-Ser has not occurred (i.e., band in lane g reacted with Anti-C1, in contrast to band in lane f), and (3) only the noncleaved, precursor form of the assembly protein (preAP)(lane g). Again, the lower abundance band above the assembly protein precursor in lane g is thought to correspond to a scarce species also detected in infected cells.

What is claimed is:

1. A recombinant DNA molecule which encodes a portion of a herpes virus proteinase precursor, said portion having the ability to cleave a herpes virus assembly protein precursor.

2. The DNA molecule of claim 1 wherein the portion of the proteinase comprises amino acids numbered 1 through 249 of simian cytomegalovirus Colbum APNG1 protein (amino acids numbered 20–268 as shown in SEQ ID NO:2) or the homologous amino acids of another herpes virus.

3. The DNA molecule of claim 1 wherein the portion of the proteinase comprises amino acids numbered 1 through 280 simian cytomegalovirus Colbum APNG1 protein (amino acids numbered 20–299 as shown in SEQ ID NO:2) or the homologous amino acids of another herpes virus.

4. The DNA molecule of claim 1 wherein the portion of the proteinase comprises the first 234 to 262 amino acids of the primary translation product of a homolog of the APNG1 gene of simian cytomegalovirus Colburn.

5. The DNA molecule of claim 1 wherein the portion of the proteinase lacks amino acids which comprise a herpes virus assembly protein precursor.

6. The DNA molecule of claim 1 which is capable of expressing said portion of the herpes virus proteinase in a host cell.

* * * * *

UNITED STATES PATENT AND TRADEMARK OFFICE
CERTIFICATE OF CORRECTION

PATENT NO.    : 6,406,902 B1                                             Page 1 of 1
DATED         : June 18, 2002
INVENTOR(S)   : D. Wade Gibson et al.

It is certified that error appears in the above-identified patent and that said Letters Patent is hereby corrected as shown below:

Column 33,
Line 39, "Colbum" has been replaced with -- Colburn --;
Line 44, "Colbum" has been replaced with -- Colburn --.

Signed and Sealed this

Fourteenth Day of January, 2003

JAMES E. ROGAN
*Director of the United States Patent and Trademark Office*

SEQUENCE LISTING

```
<160> NUMBER OF SEQ ID NOS: 41

<210> SEQ ID NO 1
<211> LENGTH: 2014
<212> TYPE: DNA
<213> ORGANISM: Simian cytomegalovirus

<400> SEQUENCE: 1
ttgtccgaca cccccaggtt attggtggtc tcgcgggggg ggaacagggg g gtttgcagg     60 cctcggttaa agagcagcac gcagatgagt ctcaagatct tgagttcttc c agccgcagg    120 gtgttgagcg gctgtccccg cgacatcttt tcgctgatct gtaatattag a tgattggca    180 caagtaaagg agaatttgcc ggttcgaacc cgggcctcct ccgtgttgga c atggccgat    240 cccgtctacg tcgggggttt tttggtgcgc tacgacgagc ctcccggaga a gctgagctg    300 tttctgccct cgggggtggt agaccgctgg ttgcgcgatt gccgaggccc g ctgcccctg    360
```

-continued

```
aatgtcaatc acgacgagtc ggcgaccgtg ggctatgtgg ctgggctcca g aatgtccgg       420 gccggcttgt tctgtttggg acgtgttacg tcccccaagt ttctggatat c gttcaaaaa      480 gcctcggaaa atccgagtt ggtgtccgg ggacctccgt ccgagtcctc g ttgcggccg        540 gacggcgtgt tggagtttct cagcggcagt tattcgggcc tgtcgctctc c agccgccga     600 gatataaacg cggccgatgg cgccgcgggc gatgcagaaa cagcgtgctt c aaacatgtg     660 gctctgtgca gcgtgggccg ccgccggggc acgttggcgg tgtatggcag g cagccagat    720 tgggtgatgg aacgtttccc ggatctcacc gaggccgacc gggaagcgct g cgaaatcag    780 ctatcgggaa gtggggaagt tgccgcgaag gaaagtgcgg aatcgtctgc c ccgccgcc     840 gtcgatccct ttcagtcgga ttcgtacggg ctgttgggga acagtgtgga c gcgctgtac    900 attcaagagc gtctccctaa gctgcgctat gacaagcggc tggtcgggt c acggctcgg     960 gagtcgtacg tgaaagccag tgtttcgccc gccgagcagg agacgtgcga t attaaagta   1020 gaaaagagc ggccgaagga gccagagcag agccacgtac cgaccgagtc a atgtctcac    1080 cctatgagcg ccgtggctac tccggcggcc tcgaccgtcg cgccttctca g gcgccgctg   1140 gcgctggccc atgacggtgt ttatttacct aaagacgctt ttttctcgct c atcggggcc   1200 agtcgtcccc tggccgaggc ggcgggagcg cgcgccgcgt atccggctgt c ccgccgcca   1260 cccgcgtatc cggtaatgaa ttatgaggac ccctcctcac gtcactttga c tacagtgcc   1320 tggctgcggc ggccagctta tgacgccgtg cctcccctgc ctcctccccc c gtcatgccc   1380 atgccgtatc gcagacgcga ccccatgatg gaggaggcca gcgcgccgc c tgggagcgc    1440 gggtacgcgc cttctgctta tgaccactac gtgaacaacg ctcctggtc g cggagccgc    1500 agcggcgcgc tcaagaggcg aagggagcgc gacgcgtcct cggatgagga a gaggacatg  1560 agttttcccg gggaagccga ccacggcaag gctcggaaaa gactcaaagc t catcacggg  1620 cgtgataata acaactctgg gagcgatgcc aagggcgatc ggtacgacga c attcgggaa  1680 gcgttacagg agctgaagcg cgagatgctg gccgtgcggc agatcgcgcc a cgtgcgctc  1740 ttggcccccg cacagctagc gacgcccgtg gcttctccga caacgaccac g tcgcatcaa  1800 gccgaggcta gcgaacctca ggcatcgact gccgctgccg cgtcgccgtc a accgcttcg  1860 tcgcacggca gcaagtcggc cgaacgcggg gtggtgaacg cctcgtgtcg c gttgcgcct  1920 ccgttggagg ctgtgaaccc ccctaaggac atggtggact gaatcgtcg c ctgtttgtg   1980 gcggcgttga ataaaatgga ataaaaactc gtac                                2014
```

<210> SEQ ID NO 2
<211> LENGTH: 609
<212> TYPE: PRT
<213> ORGANISM: Simian cytomegalovirus

<400> SEQUENCE: 2

```
Leu Ala Gln Val Lys Glu Asn Leu Pro Val A rg Thr Arg Ala Ser Ser
 1               5                  10                  15

Val Leu Asp Met Ala Asp Pro Val Tyr Val G ly Gly Phe Leu Val Arg
            20                  25                  30

Tyr Asp Glu Pro Pro Gly Glu Ala Glu Leu P he Leu Pro Ser Gly Val
        35                  40                  45

Val Asp Arg Trp Leu Arg Asp Cys Arg Gly P ro Leu Pro Leu Asn Val
    50                  55                  60

Asn His Asp Glu Ser Ala Thr Val Gly Tyr V al Ala Gly Leu Gln Asn
65                  70                  75                  80
```

-continued

Val Arg Ala Gly Leu Phe Cys Leu Gly Arg Val Thr Ser Pro Lys Phe
                    85              90              95

Leu Asp Ile Val Gln Lys Ala Ser Glu Lys Ser Glu Leu Val Ser Arg
            100             105             110

Gly Pro Pro Ser Glu Ser Ser Leu Arg Pro Asp Gly Val Leu Glu Phe
            115             120             125

Leu Ser Gly Ser Tyr Ser Gly Leu Ser Leu Ser Ser Arg Arg Asp Ile
    130             135             140

Asn Ala Ala Asp Gly Ala Ala Asp Ala Glu Thr Ala Cys Phe Lys
145             150             155             160

His Val Ala Leu Cys Ser Val Gly Arg Arg Gly Thr Leu Ala Val
            165             170             175

Tyr Gly Arg Gln Pro Asp Trp Val Met Glu Arg Phe Pro Asp Leu Thr
            180             185             190

Glu Ala Asp Arg Glu Ala Leu Arg Asn Gln Leu Ser Gly Ser Gly Glu
            195             200             205

Val Ala Ala Lys Glu Ser Ala Glu Ser Ser Ala Ala Ala Val Asp
    210             215             220

Pro Phe Gln Ser Asp Ser Tyr Gly Leu Leu Gly Asn Ser Val Asp Ala
225             230             235             240

Leu Tyr Ile Gln Glu Arg Leu Pro Lys Leu Arg Tyr Asp Lys Arg Leu
            245             250             255

Val Gly Val Thr Ala Arg Glu Ser Tyr Val Lys Ala Ser Val Ser Pro
            260             265             270

Ala Glu Gln Glu Thr Cys Asp Ile Lys Val Glu Lys Glu Arg Pro Lys
            275             280             285

Glu Pro Glu Gln Ser His Val Pro Thr Glu Ser Met Ser His Pro Met
    290             295             300

Ser Ala Val Ala Thr Pro Ala Ser Thr Val Ala Pro Ser Gln Ala
305             310             315             320

Pro Leu Ala Leu Ala His Asp Gly Val Tyr Leu Pro Lys Asp Ala Phe
            325             330             335

Phe Ser Leu Ile Gly Ala Ser Arg Pro Leu Ala Glu Ala Ala Gly Ala
            340             345             350

Arg Ala Ala Tyr Pro Ala Val Pro Pro Pro Ala Tyr Pro Val Met
            355             360             365

Asn Tyr Glu Asp Pro Ser Ser Arg His Phe Asp Tyr Ser Ala Trp Leu
    370             375             380

Arg Arg Pro Ala Tyr Asp Ala Val Pro Pro Leu Pro Pro Pro Val
385             390             395             400

Met Pro Met Pro Tyr Arg Arg Asp Pro Met Met Glu Glu Ala Glu
            405             410             415

Arg Ala Ala Trp Glu Arg Gly Tyr Ala Pro Ser Ala Tyr Asp His Tyr
            420             425             430

Val Asn Asn Gly Ser Trp Ser Arg Ser Arg Ser Gly Ala Leu Lys Arg
            435             440             445

Arg Arg Glu Arg Asp Ala Ser Ser Asp Glu Glu Asp Met Ser Phe
    450             455             460

Pro Gly Glu Ala Asp His Gly Lys Ala Arg Lys Arg Leu Lys Ala His
465             470             475             480

His Gly Arg Asp Asn Asn Ser Gly Ser Asp Ala Lys Gly Asp Arg
            485             490             495

-continued

```
Tyr Asp Asp Ile Arg Glu Ala Leu Gln Glu L eu Lys Arg Glu Met Leu
             500                 505                 510

Ala Val Arg Gln Ile Ala Pro Arg Ala Leu L eu Ala Pro Ala Gln Leu
             515                 520                 525

Ala Thr Pro Val Ala Ser Pro Thr Thr Thr T hr Ser His Gln Ala Glu
             530                 535                 540

Ala Ser Glu Pro Gln Ala Ser Thr Ala Ala A la Ala Ser Pro Ser Thr
545                 550                 555                 560

Ala Ser Ser His Gly Ser Lys Ser Ala Glu A rg Gly Val Val Asn Ala
                 565                 570                 575

Ser Cys Arg Val Ala Pro Pro Leu Glu Ala V al Asn Pro Pro Lys Asp
             580                 585                 590

Met Val Asp Leu Asn Arg Arg Leu Phe Val A la Ala Leu Asn Lys Met
             595                 600                 605

Glu

<210> SEQ ID NO 3
<211> LENGTH: 18
<212> TYPE: PRT
<213> ORGANISM: Simian cytomegalovirus

<400> SEQUENCE: 3

Ser Lys Ser Ala Glu Arg Gly Val Val Asn A la Ser Cys Arg Val Ala
  1               5                  10                 15

Pro Pro

<210> SEQ ID NO 4
<211> LENGTH: 18
<212> TYPE: PRT
<213> ORGANISM: Simian cytomegalovirus

<400> SEQUENCE: 4

Ala Glu Arg Ala Gln Ala Gly Val Val Asn A la Ser Cys Arg Leu Ala
  1               5                  10                 15

Thr Ala

<210> SEQ ID NO 5
<211> LENGTH: 18
<212> TYPE: PRT
<213> ORGANISM: Simian cytomegalovirus

<400> SEQUENCE: 5

Ser Asn Ala Glu Ala Gly Ala Leu Val Asn A la Ser Ser Ala Ala His
  1               5                  10                 15

Val Asp

<210> SEQ ID NO 6
<211> LENGTH: 53
<212> TYPE: PRT
<213> ORGANISM: Simian cytomegalovirus

<400> SEQUENCE: 6

His Ile Ser Thr His Arg Ala Ser Pro Thr H is Arg Val Ala Leu Gly
  1               5                  10                 15

Leu Tyr Gly Leu Asn Ala Ser Pro Val Ala L eu Ala Ser Asn Ala Leu
                 20                  25                 30

Ala Val Ala Leu Gly Leu Ala Leu Ala Ser G lu Arg Ser Glu Arg Leu
             35                  40                 45
```

Tyr Ser Ala Leu Ala
    50

<210> SEQ ID NO 7
<211> LENGTH: 53
<212> TYPE: PRT
<213> ORGANISM: Simian cytomegalovirus

<400> SEQUENCE: 7

Gly Leu Tyr His Ile Ser His Ile Ser Ala Arg Gly Gly Leu Tyr Leu
1               5                   10                  15

Tyr Ser Leu Tyr Ser Leu Glu Val Ala Leu Gly Leu Asn Ala Leu Ala
            20                  25                  30

Ser Glu Arg Ala Leu Ala Ser Glu Arg Gly Leu Tyr Val Ala Leu Ala
        35                  40                  45

Leu Ala Gly Leu Asn
    50

<210> SEQ ID NO 8
<211> LENGTH: 50
<212> TYPE: PRT
<213> ORGANISM: Simian cytomegalovirus

<400> SEQUENCE: 8

Ala Ser Asn Gly Leu Asn Gly Leu Ser Glu Arg Ala Leu Ala Ala Arg
1               5                   10                  15

Gly Gly Leu Thr His Arg Val Ala Leu Ala Ser Pro Ala Leu Ala Ser
            20                  25                  30

Glu Arg Met Glu Thr Pro Arg Leu Tyr Ser Ala Arg Gly Leu Glu Leu
        35                  40                  45

Tyr Ser
    50

<210> SEQ ID NO 9
<211> LENGTH: 33
<212> TYPE: PRT
<213> ORGANISM: Simian cytomegalovirus

<400> SEQUENCE: 9

Ala Leu Ala Ala Leu Ala Ser Glu Arg Pro Arg Leu Tyr Ser Pro Arg
1               5                   10                  15

Ser Glu Arg Ile Leu Glu Leu Gly Ala Ser Asn Ala Leu Ala Ser Glu
            20                  25                  30

Arg

<210> SEQ ID NO 10
<211> LENGTH: 20
<212> TYPE: PRT
<213> ORGANISM: Simian cytomegalovirus

<400> SEQUENCE: 10

Val Thr Ala Arg Glu Ser Tyr Val Lys Ala Ser Val Ser Pro Ala Glu
1               5                   10                  15

Gln Glu Thr Cys
            20

<210> SEQ ID NO 11
<211> LENGTH: 20
<212> TYPE: PRT
<213> ORGANISM: Simian cytomegalovirus

```
<400> SEQUENCE: 11

Val Thr Glu Arg Glu Ser Tyr Val Lys Ala S er Val Ser Pro Glu Ala
 1               5                  10                  15

Arg Ala Ile Leu
            20

<210> SEQ ID NO 12
<211> LENGTH: 20
<212> TYPE: PRT
<213> ORGANISM: Simian cytomegalovirus

<400> SEQUENCE: 12

Gly Ile Ala Gly His Thr Tyr Leu Gln Ala S er Glu Lys Phe Lys Met
 1               5                  10                  15

Trp Gly Ala Glu
            20

<210> SEQ ID NO 13
<211> LENGTH: 20
<212> TYPE: PRT
<213> ORGANISM: Simian cytomegalovirus

<400> SEQUENCE: 13

Gly Ile Met Gly His Val Tyr Leu Gln Ala S er Thr Gly Tyr Gly Leu
 1               5                  10                  15

Ala Arg Ile Thr
            20

<210> SEQ ID NO 14
<211> LENGTH: 20
<212> TYPE: PRT
<213> ORGANISM: Simian cytomegalovirus

<400> SEQUENCE: 14

Asn Ile Pro Ala Glu Ser Tyr Leu Lys Ala S er Asp Ala Pro Asp Leu
 1               5                  10                  15

Gln Lys Pro Asp
            20

<210> SEQ ID NO 15
<211> LENGTH: 20
<212> TYPE: PRT
<213> ORGANISM: Simian cytomegalovirus

<400> SEQUENCE: 15

Ala Val Tyr Asn Pro Lys Tyr Leu Gln Ala A sn Glu Val Ile Thr Ile
 1               5                  10                  15

Gly Ile Lys Glu
            20

<210> SEQ ID NO 16
<211> LENGTH: 17
<212> TYPE: PRT
<213> ORGANISM: Simian cytomegalovirus

<400> SEQUENCE: 16

Pro Leu Pro Leu Asn Val Asn His Asp Glu S er Ala Thr Val Gly Tyr
 1               5                  10                  15

Val

<210> SEQ ID NO 17
```

```
<211> LENGTH: 20
<212> TYPE: PRT
<213> ORGANISM: Simian cytomegalovirus

<400> SEQUENCE: 17

Phe Lys His Val Ala Leu Cys Ser Val Gly A rg Arg Arg Gly Thr Leu
 1               5                  10                  15

Ala Val Tyr Gly
            20

<210> SEQ ID NO 18
<211> LENGTH: 17
<212> TYPE: PRT
<213> ORGANISM: Simian cytomegalovirus

<400> SEQUENCE: 18

Ala Leu Pro Leu Asn Ile Asn His Asp Asp T hr Ala Val Val Gly His
 1               5                  10                  15

Val

<210> SEQ ID NO 19
<211> LENGTH: 20
<212> TYPE: PRT
<213> ORGANISM: Simian cytomegalovirus

<400> SEQUENCE: 19

Phe Lys His Val Ala Leu Cys Ser Val Gly A rg Arg Arg Gly Thr Leu
 1               5                  10                  15

Ala Val Tyr Gly
            20

<210> SEQ ID NO 20
<211> LENGTH: 17
<212> TYPE: PRT
<213> ORGANISM: Simian cytomegalovirus

<400> SEQUENCE: 20

Pro Leu Pro Ile Asn Val Asp His Arg Ala G ly Cys Glu Val Gly Arg
 1               5                  10                  15

Val

<210> SEQ ID NO 21
<211> LENGTH: 20
<212> TYPE: PRT
<213> ORGANISM: Simian cytomegalovirus

<400> SEQUENCE: 21

Phe Ala His Val Ala Leu Cys Ala Ile Gly A rg Arg Leu Gly Thr Ile
 1               5                  10                  15

Val Thr Tyr Asp
            20

<210> SEQ ID NO 22
<211> LENGTH: 17
<212> TYPE: PRT
<213> ORGANISM: Simian cytomegalovirus

<400> SEQUENCE: 22

Lys Ile Pro Ile Asn Ile Asp His Arg Lys A sp Cys Val Val Gly Glu
 1               5                  10                  15

Val
```

<210> SEQ ID NO 23
<211> LENGTH: 20
<212> TYPE: PRT
<213> ORGANISM: Simian cytomegalovirus

<400> SEQUENCE: 23

Phe Thr His Val Ala Leu Cys Val Val Gly Arg Arg Val Gly Thr Val
 1               5                  10                  15

Val Asn Tyr Asp
            20

<210> SEQ ID NO 24
<211> LENGTH: 17
<212> TYPE: PRT
<213> ORGANISM: Simian cytomegalovirus

<400> SEQUENCE: 24

Pro Leu Pro Leu Thr Val Glu His Leu Pro Asp Ala Pro Val Gly Ser
 1               5                  10                  15

Val

<210> SEQ ID NO 25
<211> LENGTH: 20
<212> TYPE: PRT
<213> ORGANISM: Simian cytomegalovirus

<400> SEQUENCE: 25

Phe Asp His Val Ser Ile Cys Ala Leu Gly Arg Arg Gly Thr Thr
 1               5                  10                  15

Ala Val Tyr Gly
            20

<210> SEQ ID NO 26
<211> LENGTH: 17
<212> TYPE: PRT
<213> ORGANISM: Simian cytomegalovirus

<400> SEQUENCE: 26

Thr Ile Pro Ile Asn Ile Asp His Glu Ser Ser Cys Val Val Gly Thr
 1               5                  10                  15

Val

<210> SEQ ID NO 27
<211> LENGTH: 20
<212> TYPE: PRT
<213> ORGANISM: Simian cytomegalovirus

<400> SEQUENCE: 27

Phe Ala His Val Ala Leu Cys Glu Leu Gly Arg Arg Glu Gly Thr Val
 1               5                  10                  15

Ala Ile Tyr Gly
            20

<210> SEQ ID NO 28
<211> LENGTH: 4
<212> TYPE: PRT
<213> ORGANISM: Simian cytomegalovirus
<220> FEATURE:
<221> NAME/KEY: VARIANT
<222> LOCATION: (1)
<223> OTHER INFORMATION: Xaa=Leu
<221> NAME/KEY: VARIANT
<222> LOCATION: (2)

```
<223> OTHER INFORMATION: Xaa=Gly, Ser, Thr, Cys, Tyr, Asn, Gln, Asp,
      Lys, Arg, Glu, or His
<221> NAME/KEY: VARIANT
<222> LOCATION: (4)
<223> OTHER INFORMATION: Xaa=Ser, Val, or As n

<400> SEQUENCE: 28

Xaa Xaa Ala Xaa
  1

<210> SEQ ID NO 29
<211> LENGTH: 4
<212> TYPE: PRT
<213> ORGANISM: Simian cytomegalovirus
<220> FEATURE:
<221> NAME/KEY: VARIANT
<222> LOCATION: (1)
<223> OTHER INFORMATION: Xaa=Val or Leu
<221> NAME/KEY: VARIANT
<222> LOCATION: (2)
<223> OTHER INFORMATION: Xaa=Gly, Ser, Thr, Cys, Tyr, Asn, Gln, Asp,
      Lys, Arg, or His
<221> NAME/KEY: VARIANT
<222> LOCATION: (4)
<223> OTHER INFORMATION: Xaa=Ser, Val, or As n

<400> SEQUENCE: 29

Xaa Xaa Ala Xaa
  1

<210> SEQ ID NO 30
<211> LENGTH: 4
<212> TYPE: PRT
<213> ORGANISM: Simian cytomegalovirus
<220> FEATURE:
<221> NAME/KEY: VARIANT
<222> LOCATION: (1)
<223> OTHER INFORMATION: Xaa=Val or Leu
<221> NAME/KEY: VARIANT
<222> LOCATION: (2)
<223> OTHER INFORMATION: Xaa=Gly, Ser, Thr, Cys, Tyr, Asn, Gln, Asp,
      Lys, Arg, Glu, or His
<221> NAME/KEY: VARIANT
<222> LOCATION: (4)
<223> OTHER INFORMATION: Xaa=Ser or Asn

<400> SEQUENCE: 30

Xaa Xaa Ala Xaa
  1

<210> SEQ ID NO 31
<211> LENGTH: 4
<212> TYPE: PRT
<213> ORGANISM: Simian cytomegalovirus
<220> FEATURE:
<221> NAME/KEY: VARIANT
<222> LOCATION: (1)
<223> OTHER INFORMATION: Xaa=Val or Leu
<221> NAME/KEY: VARIANT
<222> LOCATION: (2)
<223> OTHER INFORMATION: Xaa=Gly, Ser, Thr, Cys, Tyr, Asn, Gln, Asp,
      Glu, Lys, Arg or His
<221> NAME/KEY: VARIANT
<222> LOCATION: (4)
<223> OTHER INFORMATION: Xaa=Ser, Val, or As n

<400> SEQUENCE: 31

Xaa Xaa Ala Xaa
  1

<210> SEQ ID NO 32
```

```
<211> LENGTH: 5
<212> TYPE: PRT
<213> ORGANISM: Simian cytomegalovirus
<220> FEATURE:
<221> NAME/KEY: VARIANT
<222> LOCATION: (2)
<223> OTHER INFORMATION: Xaa=Val or Leu
<221> NAME/KEY: VARIANT
<222> LOCATION: (3)
<223> OTHER INFORMATION: Xaa=Lys or Glena
<221> NAME/KEY: VARIANT
<222> LOCATION: (5)
<223> OTHER INFORMATION: Xaa=Ser or Asn

<400> SEQUENCE: 32

Tyr Xaa Xaa Ala Xaa
 1               5

<210> SEQ ID NO 33
<211> LENGTH: 5
<212> TYPE: PRT
<213> ORGANISM: Simian cytomegalovirus
<220> FEATURE:
<221> NAME/KEY: VARIANT
<222> LOCATION: (2)
<223> OTHER INFORMATION: Xaa=Val or Leu
<221> NAME/KEY: VARIANT
<222> LOCATION: (3)
<223> OTHER INFORMATION: Xaa=Lys or Gln
<221> NAME/KEY: VARIANT
<222> LOCATION: (5)
<223> OTHER INFORMATION: Xaa=Ser or Asn

<400> SEQUENCE: 33

Tyr Xaa Xaa Ala Xaa
 1               5

<210> SEQ ID NO 34
<211> LENGTH: 4
<212> TYPE: PRT
<213> ORGANISM: Simian cytomegalovirus
<220> FEATURE:
<221> NAME/KEY: VARIANT
<222> LOCATION: (1)
<223> OTHER INFORMATION: Xaa=Val or Leu
<221> NAME/KEY: VARIANT
<222> LOCATION: (2)
<223> OTHER INFORMATION: Xaa=Gly, Ser, Thr, Cys, Tyr, Asn, Gln, Asp,
     Glu, Lys, Arg, or His
<221> NAME/KEY: VARIANT
<222> LOCATION: (4)
<223> OTHER INFORMATION: Xaa=Ser, Val, or As n

<400> SEQUENCE: 34

Xaa Xaa Ala Xaa
 1

<210> SEQ ID NO 35
<211> LENGTH: 5
<212> TYPE: PRT
<213> ORGANISM: Simian cytomegalovirus
<220> FEATURE:
<221> NAME/KEY: VARIANT
<222> LOCATION: (2)
<223> OTHER INFORMATION: Xaa=Val or Leu
<221> NAME/KEY: VARIANT
<222> LOCATION: (3)
<223> OTHER INFORMATION: Xaa=Lys or Gln
<221> NAME/KEY: VARIANT
<222> LOCATION: (5)
<223> OTHER INFORMATION: Xaa=Ser or Asn

<400> SEQUENCE: 35
```

```
Tyr Xaa Xaa Ala Xaa
 1               5

<210> SEQ ID NO 36
<211> LENGTH: 4
<212> TYPE: PRT
<213> ORGANISM: Simian cytomegalovirus
<220> FEATURE:
<221> NAME/KEY: VARIANT
<222> LOCATION: (1)
<223> OTHER INFORMATION: Xaa=Leu
<221> NAME/KEY: VARIANT
<222> LOCATION: (2)
<223> OTHER INFORMATION: Xaa=Gly, Ser, Thr, Cys, Tyr, Asn, Gln, Asp,
      Glu, Lys, Arg, or His
<221> NAME/KEY: VARIANT
<222> LOCATION: (4)
<223> OTHER INFORMATION: Xaa=Ser, Val, or As n

<400> SEQUENCE: 36

Xaa Xaa Ala Xaa
 1

<210> SEQ ID NO 37
<211> LENGTH: 4
<212> TYPE: PRT
<213> ORGANISM: Simian cytomegalovirus
<220> FEATURE:
<221> NAME/KEY: VARIANT
<222> LOCATION: (1)
<223> OTHER INFORMATION: Xaa=Val or Leu
<221> NAME/KEY: VARIANT
<222> LOCATION: (2)
<223> OTHER INFORMATION: Xaa=Gly, Ser, Thr, Cys, Tyr, Asn, Gln, Asp,
      Lys, Arg, or His
<221> NAME/KEY: VARIANT
<222> LOCATION: (4)
<223> OTHER INFORMATION: Xaa=Ser, Val, or As n

<400> SEQUENCE: 37

Xaa Xaa Ala Xaa
 1

<210> SEQ ID NO 38
<211> LENGTH: 4
<212> TYPE: PRT
<213> ORGANISM: Simian cytomegalovirus
<220> FEATURE:
<221> NAME/KEY: VARIANT
<222> LOCATION: (1)
<223> OTHER INFORMATION: Xaa=Val or Leu
<221> NAME/KEY: VARIANT
<222> LOCATION: (2)
<223> OTHER INFORMATION: Xaa=Gly, Ser, Thr, Cys, Tyr, Asn, Gln, Asp,
      Lys, Arg, Glu, or His
<221> NAME/KEY: VARIANT
<222> LOCATION: (4)
<223> OTHER INFORMATION: Xaa=Ser or Asn

<400> SEQUENCE: 38

Xaa Xaa Ala Xaa
 1

<210> SEQ ID NO 39
<211> LENGTH: 5
<212> TYPE: PRT
<213> ORGANISM: Simian cytomegalovirus
<220> FEATURE:
<221> NAME/KEY: VARIANT
<222> LOCATION: (2)
<223> OTHER INFORMATION: Xaa=Val or Leu
```

```
<221> NAME/KEY: VARIANT
<222> LOCATION: (3)
<223> OTHER INFORMATION: Xaa=
     Lys or Gln NAME/KEY: VARIANT
<222> LOCATION: (5)
<223> OTHER INFORMATION: Xaa=Ser or Asn

<400> SEQUENCE: 39

Tyr Xaa Xaa Ala Xaa
 1               5

<210> SEQ ID NO 40
<211> LENGTH: 4
<212> TYPE: PRT
<213> ORGANISM: Simian cytomegalovirus

<400> SEQUENCE: 40

Tyr Val Lys Ala
 1

<210> SEQ ID NO 41
<211> LENGTH: 5
<212> TYPE: PRT
<213> ORGANISM: Simian cytomegalovirus

<400> SEQUENCE: 41

Val Asn Ala Ser Cys
 1               5
```